United States Patent
Boschetti et al.

(10) Patent No.: US 8,305,091 B2
(45) Date of Patent: Nov. 6, 2012

(54) METHOD FOR DETERMINING THE MOISTURE CONTENT OF WOOD

(75) Inventors: Marco Boschetti, Trento (IT); Andrea Gottardo, Bressanone (IT)

(73) Assignee: Microtec S.R.L., Bressanone (IT)

( * ) Notice: Subject to any disclaimer, the term of this patent is extended or adjusted under 35 U.S.C. 154(b) by 403 days.

(21) Appl. No.: 12/719,560

(22) Filed: Mar. 8, 2010

(65) Prior Publication Data

US 2010/0225335 A1 Sep. 9, 2010

(30) Foreign Application Priority Data

Mar. 9, 2009 (IT) .............................. VR2009A0024

(51) Int. Cl.
*G01R 27/26* (2006.01)
(52) U.S. Cl. ......................... 324/664; 324/689; 324/694
(58) Field of Classification Search ................. 324/658, 324/664, 689, 694
See application file for complete search history.

(56) References Cited

U.S. PATENT DOCUMENTS

| | | | |
|---|---|---|---|
| 3,209,247 A | 9/1965 | Mead et al. | |
| 4,377,783 A * | 3/1983 | Wagner ........................ | 324/664 |
| 4,461,363 A | 7/1984 | Loy | |
| 4,468,610 A | 8/1984 | Hanson | |
| 4,683,418 A | 7/1987 | Wagner et al. | |
| 5,406,137 A | 4/1995 | Scheler et al. | |
| 6,147,503 A | 11/2000 | Nelson et al. | |
| 6,352,739 B1 | 3/2002 | Gath et al. | |
| 6,388,453 B1 | 5/2002 | Greer | |
| 6,784,671 B2 | 8/2004 | Steele et al. | |
| 7,068,050 B2 | 6/2006 | Steele et al. | |
| 2008/0161972 A1 | 7/2008 | Magill | |

FOREIGN PATENT DOCUMENTS

DE 42 26 137 A1 2/1994
WO 98/50785 A1 11/1998

OTHER PUBLICATIONS

Schajer Gary S. et al., "Measurement of wood grain angle, moisture content and density using microwaves", Holz Als Rohund Werkstoff; European Journal of Wood and Wood Products, Springer, Berlin, DE, vol. 64, No. 6, Apr. 6, 2006, pp. 483-490, XP019449257, ISSN: 1436-736X.

Trabelsi S. et al., "Practical Microwave Meter for Sensing Moisture and Density of Granular Materials", Instrumentation and Measurement Technology Conference Proceedings, 2008, IMTC 2008, IEEE, IEEE, Piscataway, NJ, USA, May 12, 2008, pp. 1021-1025, XP031274747, ISBN: 978-1-4244-1540-3.

* cited by examiner

*Primary Examiner* — Vincent Q Nguyen
(74) *Attorney, Agent, or Firm* — Pearne & Gordon LLP

(57) ABSTRACT

A method for determining the moisture content of wood (1), including the operating steps of inserting the wood (1) between a first plate and a second plate (3) of a capacitor (4); applying a first signal to the first plate (2) of the capacitor (4) using the plate as a transmitting antenna; detecting on the second plate (3) a second signal induced by the first signal, using the second plate (3) as a receiving antenna; determining from the second induced signal detected, a third reference signal, obtaining a differential signal; determining the components of the differential in phase and in quadrature signals from the first signal; filtering the components of the differential in phase and in quadrature signals to obtain a filtered in phase component and a filtered in quadrature component, which are independent of the frequency of the first signal; and calculating the moisture content of wood (1) based on the value of the filtered in phase and in quadrature components of the differential signal.

18 Claims, 4 Drawing Sheets

METHOD FOR DETERMINING THE MOISTURE CONTENT OF WOOD

This invention relates to a method for determining the moisture content of wood, and in particular a method based on the dielectric properties of the wood.

Currently, many methods are known that measure the moisture content of materials, through their dielectric properties. Some examples of these methods are described in U.S. Pat. Nos. 6,147,503, 6,388,453, 6,784,671 and 7,068,050.

In general, all known methods comprise: introducing the piece of wood (or other material), of which the moisture content must be calculated, between the first and second plate of a capacitor, usually of the flat type; applying a first signal to the first plate of the capacitor, using the plate as a transmitting antenna; detecting on the second plate a second signal induced by the first signal, using the second plate as a receiving antenna. The impedance of the capacitor with the material to be measured is then calculated based on the signal induced, and based on the impedance value (in modulus and phase), the moisture content is calculated.

However, these prior art methods have several disadvantages.

First, the impedance values obtained, allow the moisture content to be determined with poor precision.

Secondly, the prior art methods do not allow a sufficiently accurate knowledge of the distribution of moisture inside the piece of wood that, in the majority of cases, is considered as homogeneously humid.

Furthermore, the known calculation systems appear to be particularly difficult to calibrate, since they must be calibrated for each type of wood and for each size of the pieces of wood (generally the application relates to planks).

In this situation, the technical purpose of this invention is to provide a method for determining the moisture content of wood which overcomes above-mentioned disadvantages.

First and foremost, the technical purpose of this invention is to develop a method for determining the moisture content of wood that allows measurement of the moisture content with a high level of accuracy.

The second technical purpose of this invention is to provide a method for determining the moisture content of wood that allows the distribution of moisture inside the wood to be determined.

The third technical purpose of this invention is to provide a method for determining the moisture content of wood which is easier to calibrate than the prior art systems.

The technical purpose specified and the aims indicated, are mainly achieved with a method for determining the moisture content of wood as described in the appended claims.

Further characteristics and advantages of this invention will be found in the detailed description of some preferred, but not exclusive, embodiments of a method for determining the moisture content of wood, shown in the accompanying drawings, in which.

Figure 1:
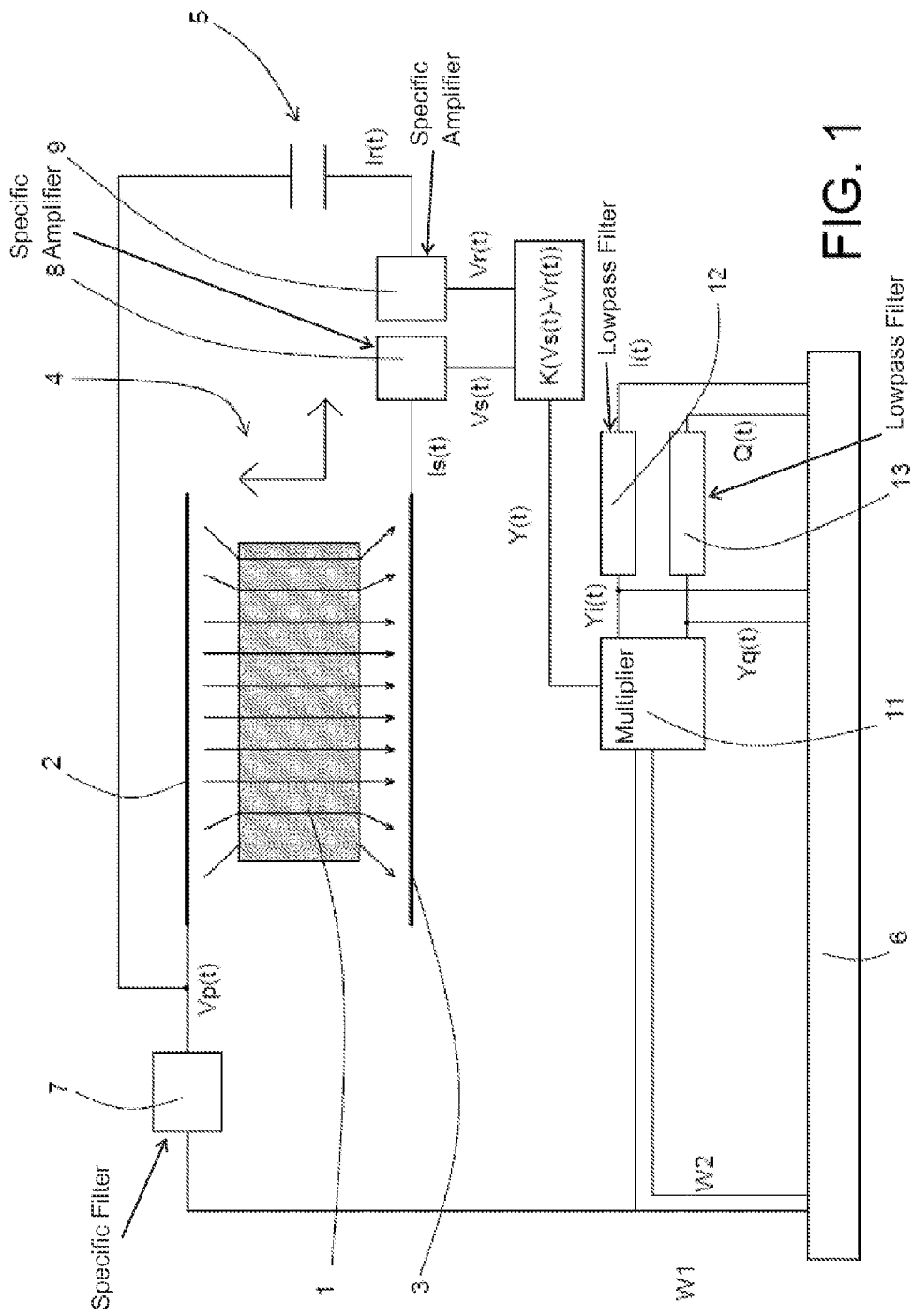
FIG. 1 shows a schematic block diagram of a possible device for implementing the method according to this invention.

Similarly to the prior art methods, the method for determining the moisture content of wood according to this invention, comprises first the operating steps of introducing each piece of wood 1 between a first and a second plate 3 of a capacitor 4, applying a first signal on the first plate 2 of the capacitor 4, using the plate as a transmitting antenna and detecting on the second plate 3 a second signal induced by the first signal, using the second plate 3 as a receiving antenna, and determining the moisture content of the wood 1, based on the value of the second induced signal detected.

In general, the plates 2, 3 used are flat plates facing each other, that can ensure the creation of a fairly uniform electromagnetic field, at least in the central area of the capacitor.

In addition, according to requirements, this invention can be implemented in a stationary way, by introducing a piece of wood 1 between the plates 2, 3, and in a dynamic way, by feeding the piece of wood 1 along a feed path that crosses the space between the two plates 2, 3 (preferred solution even if it is possible to reverse the motion by moving the plates 2, 3 in relation to the piece of wood 1).

Advantageously, in the first case, the extension of the plates 2, 3 may be are sufficiently longer than the piece of wood 1, so that the latter can be subject to a fairly uniform electromagnetic field. This configuration allows measurement of the average moisture of the piece of wood 1.

In contrast, with the dynamic measurement, the pieces of wood 1 should be pushed along a main direction (in the case of planks, along their longitudinal axis) and the plates 2, 3 should be of size such that they cover only a specific section of each piece of wood 1. In particular, this can be achieved by using plates 2, 3 which are sufficiently bigger than the planks transversally to the feed path, but smaller than the planks parallel with the feed path (in any case, preferably they are big enough to ensure a fairly uniform magnetic field, at least in the central area).

By operating this way, it is possible to determine the average moisture not of the entire piece of wood 1, but of each transversal section between the two plates 2, 3.

According to this invention, the moisture is not determined based on the simple second signal induced.

The method according to this invention also comprising the operating step of detecting from the second induced signal detected a third reference signal, in order to obtain a differential signal.

As an advantage, the third reference signal corresponds approximately to the induced signal detected on the second plate 3 in the absence of wood 1 (equally to the first signal applied to the first plate 2). For simplicity, the third signal can be generated with a second reference capacitor 5 with capacity more or less corresponding to the no-load capacity of the measurement system adopted.

Note that for the purposes of this invention, it is not important so much that the third signal is exactly the same as the signal obtained with no-load, but that it is similar to it.

Thanks to this precaution, it is possible to determine the moisture content, not based on the entire second signal induced in the presence of wood 1, but with reference (at least in a first approximation) only to the variation of the second signal induced on the second plate 3, in case of no-load.

The subsequent steps of this invention consist of determining the in phase and quadrature components of the differential signal in relation to the first signal applied to the first plate 2, and filtering these in phase and quadrature components of the differential signal, to obtain a filtered in phase component and a filtered in quadrature component, which are independent from the frequency of the first signal. This can normally be obtained with a low-pass filter.

Finally, the method involves calculating the moisture content of the wood 1 based on the value of the filtered in phase and in quadrature components of the differential signal (in particular, according to the methods indicated below).

Figure 2:
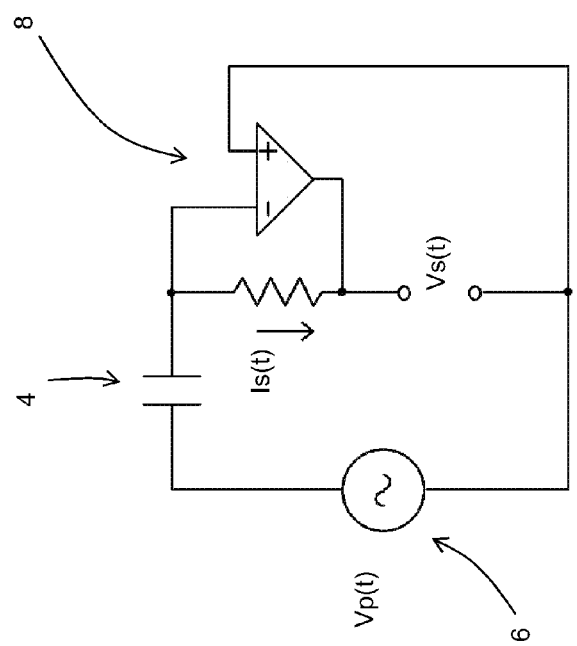
FIG. 2 shows a schematic view of an electric circuit able to implement a step of the method according to this invention.
Figure 3:
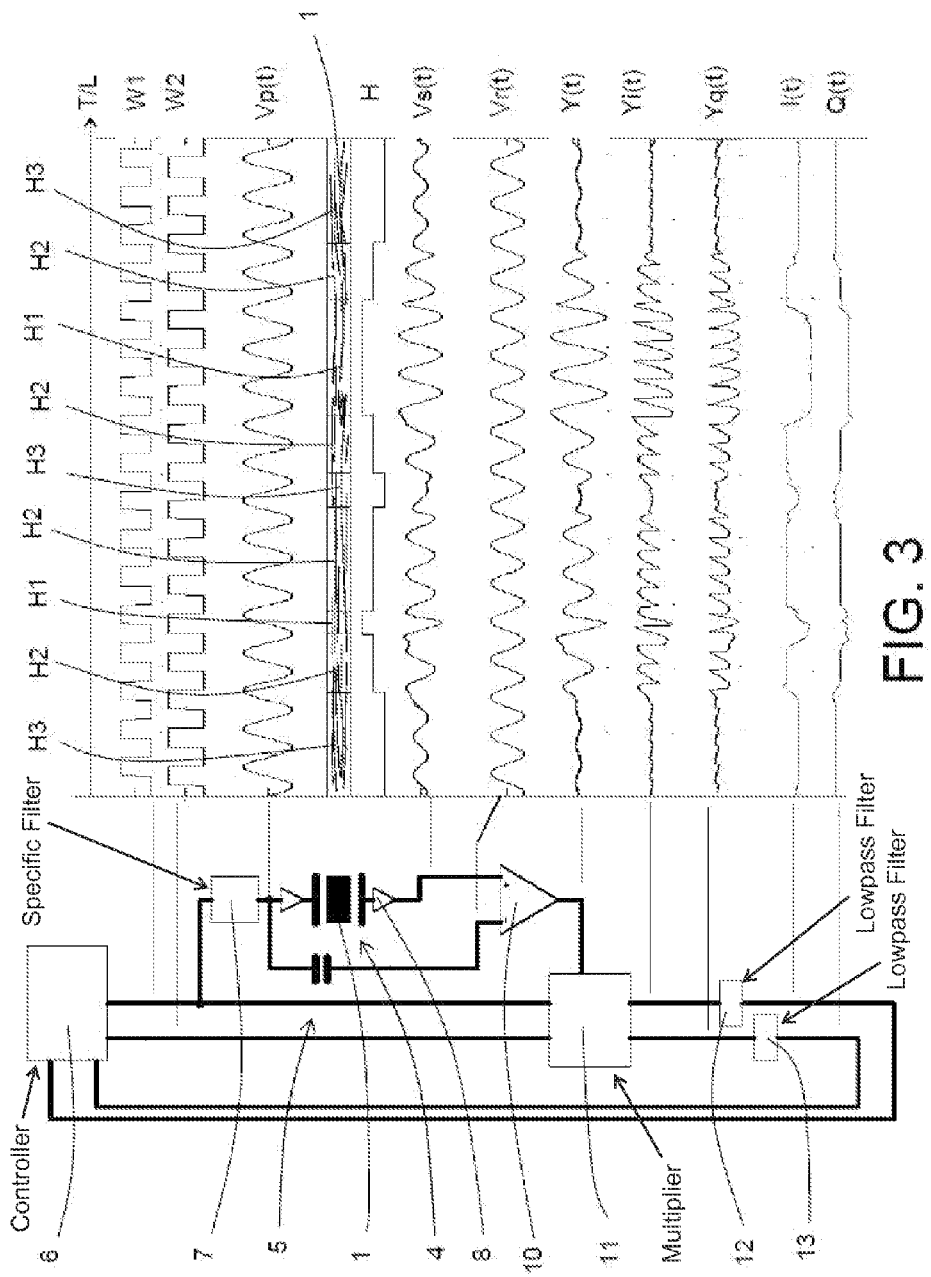
FIG. 3 shows a different schematic block diagram of a device able to implement the method according to this invention, alongside a qualitative representation of the wave forms of the different signals used/detected in the various steps of the method according to this invention.

The foregoing operating steps are shown in FIGS. 1 to 3.

In particular, FIGS. 1 and 3 show the block-diagram of two pieces of electric/electronic equipment (very similar to each other) able to implement the method according to this invention. Note that the equipment of FIG. 3 is explicitly intended to dynamically measure the moisture content of the planks moving in relation to plates 2, 3.

The operation of the entire system is managed by a controller 6 that generates first of all, two carrier square waves (in voltage) W1, W2, where the first W1 constitutes the reference carrier wave while the second wave W2 is in quadrature (phase in advance by 90 degrees) compared to the first W1. As an advantage, the two carriers have a frequency within a range from 10 KHz and 50 KHz.

Through a specific filter 7, a sinusoidal voltage signal Vp(t) is obtained from the reference carrier wave P1, to apply to the first transmitting plate 2.

An induced current Is(t) is therefore generated on the second plate 3, from which a voltage signal Vs(t) (second signal) is obtained through a specific amplifier 8, as shown in FIG. 2.

In addition to the first plate 2, the voltage Vp(t) is also applied to a reference capacitor 5 with capacity corresponding to about the no-load capacity of the first and second plate 3 added together. Similarly to what occurs on the second plate 3, the reference capacitor 5 also allows a certain induced current Ir(t) to be determined that generates a voltage signal Vr(t), once it is converted into voltage through a specific amplifier 9 (similar to the one shown in FIG. 2).

At this point, in an adder 10, the reference voltage Vr(t) is subtracted from the measured voltage Vs(t), thus obtaining a signal which substantially corresponds to the impedance variation produced by the presence of wood 1. Since this signal is small compared to the others, during subtraction, this is suitably amplified (by a factor K), thus obtaining the differential signal Y(t).

The following step is to determine for this differential signal Y(t) the in phase and in quadrature components of the first signal (in relation to the reference carrier wave W1). According to this preferred embodiment of this invention, the two components of the differential signal Y(t) are obtained by a multiplier 11, multiplying the carrier signal for the first carrier wave W1 and second carrier wave W2 respectively, obtaining two signals Yi(t) and Yq(t).

In the following step, the two signals Yi(t) and Yq(t) just obtained are filtered with low-pass filters 12, 13 (the preferred band used is 1 KHz) to obtain two filtered in phase I(t) and in quadrature Q(t) components of the differential signal Y(t), components that are proportional to the complex impedance variation due to the introduction of wood 1 between the two plates 2, 3 of the capacitor 4.

An example of the wave forms that can be obtained is shown in FIG. 3 that represents in qualitative terms how the method according to this invention works, with reference to a wood plank which is fed axially between the two plates 2, 3 with constant speed.

As a consequence, the abscissa of the different graphs indicates the time T and the position along the plank L.

As it can also be noticed, the plank shows alternating areas H1 with high moisture content, areas H2 with average moisture content and areas H3 with low moisture content.

Finally, the last two graphs of FIG. 3 show the value of the filtered in phase I(t) and in quadrature Q(t) components of the differential signal along the plank.

The degree of moisture of each section of the plank is then determined based on the instantaneous values of the filtered in phase I(t) and in quadrature Q(t) components of the differential signal.

Figure 4:
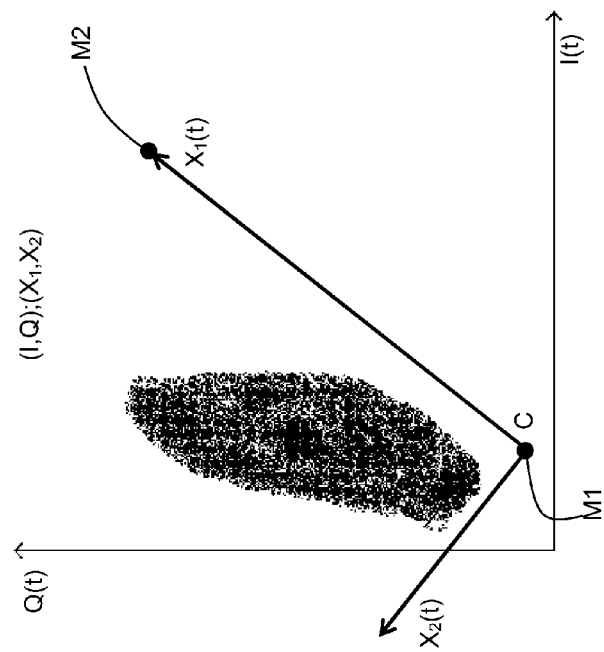
FIG. 4 shows a graph which represents some phases of the method according to this invention.

FIG. 4 shows a first Cartesian reference system, whose coordinates are: in abscissa, the filtered in phase component I(t) and in ordinate, the filtered in quadrature component Q(t). In addition, this Figure shows the spot of the possible points that can be identified for the filtered components I(t) and Q(t), for a group of planks with typical moisture and density.

Nonetheless, this reference system does not constitute an optimal basis to evaluate the moisture, since the differential signal Y(t) is affected not only by the presence of wood 1, but also by the variation of the conditions of the surrounding environment (such as temperature and moisture of the air surrounding the measurement area, the presence of electric or electronic devices, the presence of conductive and/or ferromagnetic materials, etc).

Consequently, the preferred embodiment of this invention comprises, prior to the step of calculating the moisture, an operating step of correcting the filtered in phase and in quadrature components, based on the ambient conditions. This correction step comprises in particular, the correction of filtered in phase I(t) and in quadrature Q(t) components based on a first preliminary measurement M1 taken by detecting the second signal without wood 1, and a second preliminary measurement M2 taken by detecting the second signal in the absence of the first signal. The first preliminary measurement M1 and the second preliminary measurement M2 are preferably taken before starting the examination of each piece of wood 1.

Based on these preliminary measurements, the preferred method according to this invention comprises the identification in the first reference system, of a second reference system which is independent of the ambient conditions and identified by the position, in the first reference system, of the differential signals detected in the first and second preliminary measurement M2.

In particular, the second reference system is chosen with centre C in the point representing the first preliminary measurement M1 in the first reference system.

In addition, in the embodiment shown in FIG. 4, the second reference system is also an orthogonal Cartesian system $(X_1(t), X_2(t))$ with a first reference axis exiting the centre C just defined and passing through the reference point of the second preliminary measurement M2, in the first reference system.

Once the second reference system has been introduced, a point with coordinates I, Q in the first reference system, has coordinates $X_1, X_2$ in the second reference system.

At this point, it is finally possible to determine the relative moisture content of wood 1, with the formula below:

$$\text{moisture} = f(X_1, X_2)$$

in particular, according to the preferred embodiment of this invention, the above formula takes the form:

$$\text{moisture} = \sum_{k=-2}^{2} a_k X_1^k + \sum_{k=-2}^{2} b_k X_2^k + c \tag{1.1}$$

where $a_k$, $b_k$, and c are parameters which depend on the configuration of the system and that must be determined previously, during the calibration phase of the system used.

The model used can be indeed calibrated, measuring a group of samples of wood 1, with the measuring system that will be used later on, and with a known independent system able to calculate the water content of the samples. For example, an independent system can be the dry system, which consists of weighing the sample, drying it completely in an oven until the water has completely evaporated, and then weighing the sample again. In this system, the relative moisture is then defined as:

$$\text{moisture} = \frac{(P - Ps)}{Ps} \tag{1.2}$$

where P is the initial weight and Ps is the dry weight.

Although this system has the disadvantage of being time consuming and destructive, it defines the moisture content of the wood.

The system just described has the disadvantage of requiring a large number of independent measurements to perform calibration, since a different model, and therefore a plurality of measurements, are needed for each size of the samples (size: thickness and width of the planks in the dynamic system; thickness, width and length of the planks in the stationary system).

In the preferred embodiment among those developed so far, the method according to this invention is independent of the sizes of the sample measured. In this way, it is possible to calibrate the measurement system for a certain section (width by thickness and if necessary by length) and therefore obtain the other sizes from the reference section.

Figure 5:
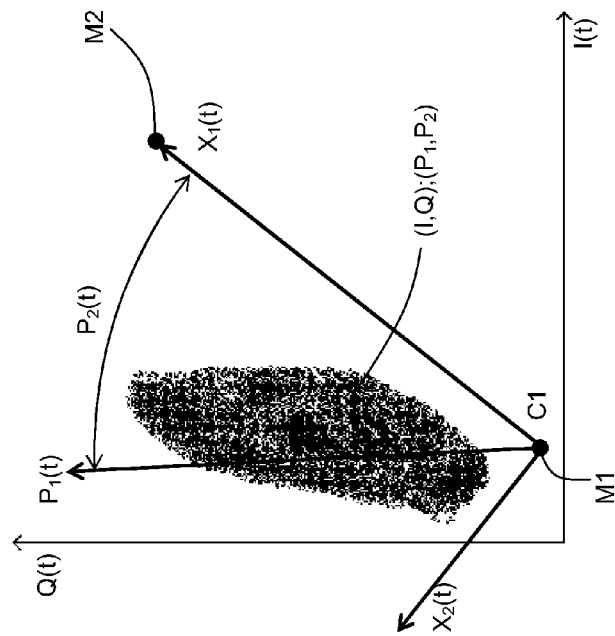
FIG. 5 shows a second graph which represents some phases of a different embodiment of the method according to this invention.

This solution is shown in FIG. 5.

In this case, the second reference system adopted is a polar reference system whose centre C1 for the measurement of the radial coordinate $P_1(t)$ is always defined by the indicative point of the first preliminary measurement M1 in the first Cartesian reference system, and the reference straight line for the measurement of the angular coordinate $P_2(t)$ is defined by the straight line exiting from the centre C1 and passing through the indicative point of the second preliminary measurement M2 in the first Cartesian reference system.

In order to render the method independent from the transversal dimensions of the planks analysed, the relative moisture is calculated again with the formula $$\text{moisture} = \sum_{k=-2}^{2} a_k X_{1k} + \sum_{k=-2}^{2} b_k X_{2k} + c \tag{2.1}$$

but in this case, variables $X_1$ and $X_2$ are no longer the Cartesian coordinates in the second reference system, but they are expressed by the formulas:

$$X_1 = P_1'^* \cos(P_2') \tag{2.2}$$

$$X_2 = P_1'^* \sin(P_2') \tag{2.3}$$

where $P_1'$ and $P_2'$ are in turn calculated with formulas:

$$P_1' = \sum_{k=0}^{2} a_{1k} P_1^k + \sum_{k=0}^{2} b_{1k} P_2^k + c_1 \tag{2.4}$$

$$P_2' = \sum_{k=0}^{2} a_{2k} P_1^k + \sum_{k=0}^{2} b_{2k} P_2^k + c_2 \tag{2.5}$$

where $a_{1k}$, $b_{1k}$, $c_1$, $a_{2k}$, $b_{2k}$ and $c_2$ are parameters which depend on the configuration of the measurement system adopted and the dimensions of the wood 1, measured in relation to a reference sample, and $P_1$ and $P_2$ are the radial and angular coordinates respectively, which express the position of the filtered differential signal (I,Q) in relation to the second polar reference system.

Using this calculation system, it is therefore possible to calibrate the system, by simply calculating the coefficients of the formula (2.1) for a single dimension of the piece of wood 1, and relate all the other measurements to the measurement thus calculated, transforming the polar coordinates $P_1$ and $P_2$ into coordinates $P_1'$ and $P_2'$.

With regard to the dynamic method of implementing the method according to this invention, the tests carried out allowed to determine that, in case of limited variations of the sizes of the section compared to the calibration values, all coefficients of formulas (2.4) and (2.5) are 0, except for $a_{11}$ and $a_{21}$ which are:

$$a_{11} = \frac{wid0 * thi0}{wid * thi} \tag{2.6}$$

$$a_{21} = 1 \tag{2.7}$$

where wid and thi are the width and thickness values of the piece of wood 1 currently measured, and wid0 and thi0 are the corresponding reference dimensions of the piece of wood 1, with which the measurement system was calibrated. In other words, the transformation is reduced to a scale factor of variable P1, since:

$$P1' = P1 * \frac{wid0 * thi0}{wid * thi} \tag{2.8}$$

$$P2' = P2 \tag{2.9}$$

This invention has important advantages.

First, the method for determining the moisture content of wood 1 according to this invention allows measurement of the moisture content with a high level of accuracy, thanks to the solution using the differential signal as a reference value.

Secondly, when the method is implemented dynamically, it allows the distribution of moisture inside the wood 1 to be determined.

Third, when the criteria for evaluating the moisture content of the wood 1 using the formulas from (2.1) to (2.5) is adopted, the method according to this invention allows a simpler calibration phase than in prior art systems.

It should also be noticed that this innovation is fairly easy to produce and the cost for implementing the invention is not very high.

The invention described above may be modified and adapted in several ways without thereby departing from the scope of the inventive concept. All details of the invention may be substituted by other technically equivalent elements and in practice, all the materials used, shapes and sizes of the various components, may vary according to requirements.

The invention claimed is:

1. A method for determining the moisture content of wood (1), comprising the operating steps of:
    inserting the wood (1) between a first plate and a second plate (3) of a capacitor (4);
    applying a first signal to the first plate (2) of the capacitor (4) using the plate as a transmitting antenna;

detecting on the second plate (3) a second signal induced by the first signal, using the second plate (3) as a receiving antenna; and determining the moisture content of the wood (1) based on the value of the second, induced signal detected;

the method being characterised in that it also comprises the operating steps of:

taking from the second, induced signal detected a third reference signal, obtaining a differential signal;

determining the components of the differential signal in phase and in quadrature relative to the first signal;

filtering the components of the differential signal in phase and in quadrature to obtain a filtered in phase component and a filtered in quadrature component which are substantially independent of the frequency of the first signal; and calculating the moisture value for the wood (1) based on the value of the filtered in phase and in quadrature components of the differential signal.

2. The method according to claim 1, characterised in that it also comprises, before the step of calculating the moisture, an operating step of correcting the filtered in phase and in quadrature components according to the ambient conditions.

3. The method according to claim 2, characterised in that the correcting step involves correction of the filtered in phase and in quadrature components based on a first advance measurement (M1) taken by detecting the second signal in the absence of the wood (1), and a second advance measurement (M2) taken by detecting the second signal in the absence of the first signal.

4. The method according to claim 3, characterised in that it also involves the operating step of at least implicitly showing the differential signal in a first reference system of coordinates corresponding to the filtered in phase component and to the filtered in quadrature component of the differential signal, and also being characterised in that in the first reference system a second reference system is identified by the position, in the first reference system, of the differential signals detected in the first advance measurement and the second advance measurement (M2).

5. The method according to claim 4, characterised in that the second reference system is selected with the centre at the point representing the first advance measurement (M1) in the first reference system.

6. The method according to claim 5, characterised in that the second reference system has a first reference axis exiting the centre and passing through the point representing the second advance measurement (M2) in the first reference system.

7. The method according to claim 3 characterised in that the moisture content of the wood (1) is determined continuously by feeding the wood (1) along a feed path along which the plates (2, 3) are positioned, and in that the first advance measurement (M1) and the second advance measurement (M2) are repeated with the passage of time so as to dynamically adjust the measurements to variations in the external conditions.

8. The method according to claim 7, characterised in that the first advance measurement (M1) and the second advance measurement (M2) are taken before determining the moisture content of each piece of wood (1).

9. The method according to claim 4, characterised in that the first reference system is a Cartesian coordinate system.

10. The method according to claims 9 characterised in that the moisture value is obtained from the filtered in phase and in quadrature components of the differential signal using a formula:

$$\text{moisture} = \sum_{k=-2}^{2} a_k X_1^k + \sum_{k=-2}^{2} b_k X_2^k + c$$

where $a_k$, $b_k$, and c are parameters which depend on the system configuration, and $X_1$ and $X_2$ are values obtained respectively from the filtered in phase and in quadrature components of the differential signal, and in that the second reference system is a Cartesian coordinate system and also being characterised in that the variables $X_1$ and $X_2$ correspond to the coordinates in the second reference system of the point representing the differential signal.

11. The method according to claims 9 characterised in that the moisture value is obtained from the filtered in phase and in quadrature components of the differential signal using a formula:

$$\text{moisture} = \sum_{k=-2}^{2} a_k X_1^k + \sum_{k=-2}^{2} b_k X_2^k + c$$

where $a_k$, $b_k$, and c are parameters which depend on the system configuration, and $X_1$ and $X_2$ are values obtained respectively from the filtered in phase and in quadrature components of the differential signal, and in that the second reference system is a polar coordinate system and also being characterised in that it also comprises an operating step of calculating the values $X_1$ and $X_2$ with the formula:

$X_1 = P_1' * \cos(P_2')$ $X_2 = P_1' * \sin(P_2')$ where $P_1'$ and $P_2'$ are calculated with the formulae:

$$P_1' = \sum_{k=0}^{2} a_{1k} P_1^k + \sum_{k=0}^{2} b_{1k} P_2^k + c_1$$

$$P_2' = \sum_{k=0}^{2} a_{2k} P_1^k + \sum_{k=0}^{2} b_{2k} P_2^k + c_2$$

in which $a_{1k}$, $b_{1k}$, $c_1$, $a_{2k}$, $b_{2k}$ and $c_2$ are parameters which depend on the configuration of the measuring system adopted and the dimensions of the wood (1) compared with a reference sample, and $P_1$ and $P_2$ are respectively the radial coordinate and the angular coordinate expressing the position of the filtered differential signal relative to the second reference system.

12. The method according to claim 1, characterised in that the moisture value is obtained from the filtered in phase and in quadrature components of the differential signal using a formula:

$$\text{moisture} = \sum_{k=-2}^{2} a_k X_1^k + \sum_{k=-2}^{2} b_k X_2^k + c$$

where $a_k$, $b_k$, and c are parameters which depend on the system configuration, and $X_1$ and $X_2$ are values obtained respectively from the filtered in phase and in quadrature components of the differential signal.

13. The method according to claim 12, characterised in that the parameters $a_k$, $b_k$, and c are determined in advance at the calibration stage for the system used.

14. The method according to claim 1, characterised in that the third reference signal corresponds, in a first approximation, to the second signal which may be detected on the second plate (3) in the absence of wood (1), the first signal applied to the first plate (2) being equal.

15. The method according to claim 1, characterised in that the first signal is a sinusoidal voltage.

16. The method according to claim 15, characterised in that the first signal is obtained starting with a carrier signal consisting of a square wave.

17. The method according to claim 16, characterised in that the in phase and in quadrature components of the differential signal are obtained by multiplying the differential signal respectively by the carrier signal and by a signal equal to the carrier signal and in quadrature with it.

18. The method according to claim 1, characterised in that the moisture content of the wood (1) is determined continuously by feeding the wood (1) along a feed path along which the plates (2, 3) are positioned.

* * * * *